(12) United States Patent
Caragine et al.

(10) Patent No.: US 9,200,321 B2
(45) Date of Patent: Dec. 1, 2015

(54) DEVICE AND KIT FOR COLLECTING FORENSIC DNA FROM SURFACES INCLUDING FINGERPRINTS

(75) Inventors: Theresa A. Caragine, New York, NY (US); Mechthild Prinz, New York, NY (US); James A. Sebestyen, Astoria, NY (US); Robert Shaler, Flemington, NJ (US)

(73) Assignee: City of New York, By And Through Its Office Of Chief Medical Examiner, New York, NY (US)

( * ) Notice: Subject to any disclaimer, the term of this patent is extended or adjusted under 35 U.S.C. 154(b) by 348 days.

(21) Appl. No.: 12/258,272

(22) Filed: Oct. 24, 2008

(65) Prior Publication Data

US 2009/0098559 A1    Apr. 16, 2009

Related U.S. Application Data

(63) Continuation of application No. 11/884,807, filed as application No. PCT/US2006/006302 on Feb. 21, 2006, now abandoned.

(60) Provisional application No. 60/655,206, filed on Feb. 20, 2005.

(51) Int. Cl.
| | |
|---|---|
| *C12Q 1/68* | (2006.01) |
| *A61B 10/00* | (2006.01) |
| *G01N 1/02* | (2006.01) |
| *G01N 1/00* | (2006.01) |

(52) U.S. Cl.
CPC ............... *C12Q 1/6876* (2013.01); *A61B 10/00* (2013.01); *A61B 10/0096* (2013.01); *G01N 1/02* (2013.01); *A61B 10/0045* (2013.01); *C12Q 2600/156* (2013.01); *G01N 2001/007* (2013.01); *G01N 2001/028* (2013.01)

(58) Field of Classification Search
CPC ............... A61B 10/00; A61B 10/0045; A61B 10/0096; C12Q 1/6876; C12Q 2600/156; G01N 1/02; G01N 2001/007; G01N 2001/028
See application file for complete search history.

(56) References Cited

U.S. PATENT DOCUMENTS

| | | | | |
|---|---|---|---|---|
| 4,752,985 A | * | 6/1988 | Quearry et al. | ............ 15/229.1 |
| 5,910,420 A | * | 6/1999 | Tuompo et al. | ............ 435/18 |
| 6,779,665 B2 | | 8/2004 | Bolanos | |

OTHER PUBLICATIONS

Schultz et al., Archived or directly swabbed latent fingerprints as a DNA source for STR typing, Forensic Science International 127 (2002) 128-130.*
Oorschot et al., Are you collecting all the available DNA from touched objects?, International Congress Series 1239 (2003) 807-803.*
2009 DIE NET for Source: Webster's Revised Unabridged Dictionary (1913) for "swab" via die.net, Online. Jul. 16, 2009 <http://dictionary.die.net/swab>.*

(Continued)

*Primary Examiner* — Young J Kim
(74) *Attorney, Agent, or Firm* — Katten Muchin Rosenman LLP (57) ABSTRACT

The present invention relates to a high sensitivity crime scene swab device for maximal recovery of trace forensic DNA evidence left at a crime scene for DNA PCR analysis. More particularly, DNA recovery is obtained from fingerprints lifted from surfaces at the crime scene. The invention also relates to a high sensitivity method for DNA analysis of trace DNA obtained by generating small tandem repeat (STR) profiles using a polymerase chain reaction protocol.

23 Claims, 8 Drawing Sheets

(56) References Cited

OTHER PUBLICATIONS

Merriam Webster's Collegiate Dictionary. 11th ed. 2003, definitions of "swab" and "cloth".*
Grolier Multimedia Encyclopedia. 2009. for "rope" as known in 1869, Online. Jul. 16, 2009 <http://gme.grolier.com/cgi-bin/article?assetid=0250250-0>.*
Oorschot et al., DNA fingerprints from fingerprints, Nature, vol. 387, Jun. 19, 1997, pp. 767 and 768.*
MacWhatley, Cotton Textile Manufacturing Processes, 2009, pp. 1-98, retrieved from http://randolphhistory.wordpress.com/.*
Celanese, Complete Textile Glossary, pp. 1-210, © 2001. Copyright Celanese Acetate LLC. All Rights Reserved.*
Turner et al. DNA Forensic Evidence. Police Executive Research Forum 2002.*
Bober et al. DNA Fingerprinting. Worcester Polytechnic Institute (2004):1-51.*
Pesaresi et al. Qualitative and quantitative analysis of DNA recovered from fingerprints. International Congress Series 2003;1239:947-51.*
Caragine, T. et al. "Improvements to a High Throughput Strategy for STR Typing of DNA from Fingerprints and Trace Evidence.", www.promega.com/products/pm/genetic-identy/ishi-conference-proceedings/14th-ishi-oral-presentations/, 14th International Symposium on Human Identification Oral Presentations (2003), 2 pages.

* cited by examiner

DEVICE AND KIT FOR COLLECTING FORENSIC DNA FROM SURFACES INCLUDING FINGERPRINTS

CROSS-REFERENCE TO RELATED APPLICATIONS

This application is a Continuation of U.S. patent application Ser. No. 11/884,807, filed Aug. 20, 2007, now abandoned which is a 371 of International Patent Application No. PCT/US2006/006302, filed Feb. 21, 2006, which claims priority to U.S. Provisional Patent Application No. 60/655,206, filed Feb. 20, 2005. The contents of these applications are hereby incorporated by reference in their entireties.

FIELD OF THE INVENTION

The present invention relates to a high sensitivity crime scene swab device for maximal recovery of trace forensic DNA evidence left at a crime scene for DNA PCR analysis. More particularly, DNA recovery is obtained from fingerprints lifted from surfaces at the crime scene. The invention also relates to a high sensitivity method for DNA analysis of trace DNA obtained by generating small tandem repeat (STR) profiles using a polymerase chain reaction protocol that is capable of amplifying DNA from about two to about four cells or about 12.5 to about 25 pg DNA.

BACKGROUND

Property crimes, such as theft, burglary, and arson, make up an overwhelming majority of all crimes. Property criminals are often recidivists. According to data from the Virginia State database, 32% of the violent crimes solved in Virginia were committed by individuals with previous property crime convictions. (See, Ban, J. Cambridge Healthtech Institute's Fifth Annual DNA Forensics. Washington D.C., Jun. 27-28, 2002.)

Fingerprints were first used in the United States by the New York prison system in 1903. Although, it is often considered by many as a "low-tech" crime-solving method because it entails subjective visual examination, it is a highly reliable and accessible means of obtaining evidence at a crime scene. Today, the fingerprinting technique incorporates highly sophisticated state of the art technologies. To date, the FBI has a large collection of fingerprints, totaling millions, which have been used by law enforcement agencies to identify defendants and crime victims by matching prints from crime scenes with those on file.

The basic principle behind the use of fingerprint evidence are based on, (1) a person's "friction ridge patterns" or swirled skin on his/her fingertips do not change, and (2) no two persons have the same pattern of friction ridges. Since the friction ridges contain rows of sweat pores, fingerprints are often produced when the sweat from these ridges mixed with other body oils and dirt. The visibility of the prints is enhanced only when powders and chemicals are dusted onto the surface and excess powder brushed away, lifted from the surface using tapes or photographed and then compared to fingerprints in a database. Prints may be visible with alternate light sources or with the naked eye depending upon the surface and the situation. For example, in a humid environment, more moisture on the skin would allow for a more visible print.

The quality of the prints, therefore, depends on the type of surfaces from which they are lifted. Furthermore, fingerprints are often lost with time or through contamination by the first responders (e.g., a fingerprint collector) at the scene of crime, resulting in the destruction or rendering useless of valuable evidences. In addition, because it is almost impossible to determine the age of a set of fingerprints, defendants often attempt to testify that they were present prior to the crime and the prints were left at a time other than at the time of the crime. Although computer enhancement laser techniques have been employed to extrapolate complete prints from mere fragments and invisible markings respectively, there is still a need for a better and more sensitive method of identifying the perpetrator.

The use of DNA analysis or typing has proven to be a revolutionary and powerful method for solving crimes, particularly in violent crimes since the introduction of fingerprinting a century ago. Being the genetic blueprint, each individual's DNA is unique to them except for identical twins. As such, DNA analysis is a highly discriminating method of identifying individuals. The value of forensic DNA analysis is enormous, particularly, with the creation of a national DNA database management system, known as CODIS (Combine DNA Index System) set up by the FBI and the U.S. Department of Justice. CODIS contains DNA profiles from biological evidence collected from crimes scenes as well as from convicted offenders. The profile generated from an evidentiary sample may be searched against the profiles contained in CODIS, in order to link evidence from other crimes to the case, or if no suspect is known, to a matching profile from a previous offender. Therefore, evidence from different crime scenes can be compared to link the same perpetrator to multiple crimes locally, nationally or internationally. Furthermore, the DNA molecule is very stable and can withstand significant environmental insults or challenges, thus allowing information to be collected from old biological samples or badly degraded samples.

Forensic DNA samples are usually collected from blood, saliva, semen, and other bodily fluids by wiping onto a cotton-tipped swab or a cotton pad. Other sources include hair, bones, skin etc. The evidence-containing swabs or pads are placed into plastic or paper container or bag for future analysis. One of the major disadvantages of using a cotton-tipped swab or cotton pad is that elution of small samples from the cotton-tipped swab or cotton swab can be inefficient in recovery and release of DNA, particularly when the amount available is small to begin with. Furthermore, the amount of sample evidence may be contaminated or diminished when the swab or pad comes in contact with the container or bag.

DNA samples are extracted, PCR-amplified and traditionally analyzed by restriction fragment length polymorphism (RFLP). RFLP is a technique by which an individual of a species can be differentiated by the banding pattern of DNA fragments obtained by subjecting DNA to restriction enzyme cleavage. (See, Wyman, A. R and White, R., *Proc. Natl. Acad. Sci. USA* 77, 6754 (1980)). The unique banding patterns of the DNA fragments are then separated by gel electrophoresis and detected by Southern blot analyses using a radioactive probe for a particular locus of the human chromosome, such as the D14S1 locus, which serves as a polymorphic marker unique to an individual. Two major disadvantages of the RFLP technique are the requirement for a substantial amount of DNA is required that is not degraded or fragmented. If a small quantity amount of DNA is analyzed, multiple cycles of amplification must be performed in order to obtain sufficient DNA for RFLP analysis. Thus, if low quantity DNA is obtained, the RFLP method can be burdensome and time consuming, in addition to the added cost in carrying out multiple PCR reactions.

More recently, the use of tandemly repeated DNA sequences, which are widespread throughout the human genome with sufficient variability amongst individuals in a population, provide still a further advancement in forensic DNA evidence analysis. Depending on the size of the tandem repeats, these tandemly repeated DNA regions may be classified as minisatellites, or variable number of tandem repeats (VNTRs) having core repeats of about 9-80 base pairs (bp) in length (See, Jeffreys, A. J., et al., Nature 316, 76 (1985)) or microsatellites, or short tandem repeats (STRs) with about 2-5 bp repeats (See, Weber, J. L. and May, P. E., Am. J. Hum. Genet. 44, 388 (1989); Edwards, A., et al., Am. J. Hum. Genet. 49, 746 (1991) and Polymeropoulos, M. H. et al., Nucl. Acids. Res. 19, 4018; and id. 4306m (1991)).

Although STRs have the same basic structure as VNTRs, the tandemly repeated sequences of 2-5 bp make the STR markers more compatible with the use of PCR. In addition, only a limited number of selected STR markers that are useful for human identification are required in forensic analyses compared to the thousands that are available. Criteria for selection of STR markers include (1) high degree of variability within the population, (2) easily distinguishable amplified products, (3) low prevalence of stutter bands, which are amplification artifacts that are one or more repeat lengths above or below the true amplified alleles, and (4) low mutation rates. (See, Weber, J. L. and May, P. E., Am. J. Hum. Genet. 44, 388 (1989); Levinson, G. and Gutman, G. A., Mol. Biol. Evol. 4, 203 (1987) and Schlotterer, C. and Tautz, D., Nucl. Acids. Res. 20, 211 (1992)). Thus, STR systems that are currently being developed must have high discrimination potential with minimal genetic artifacts, such as microvariants, and minimal amplification artifacts, e.g. stutter bands. Many STR loci are in development as genetic markers for forensic purposes with several more to be expected. (See, Schumm, J. W., Notes Magazine 58, 12 (1996) Promega).

Both the fingerprinting and DNA typing methods are powerful means currently used for solving crimes. Thus, combining both these methods may prove to be a major advance in the field of forensic science for the detection and identification of suspects, with a low possibility of mistaken identities. However, both methods require a means of collecting forensic evidence at the crime scene that are not compromised and the method must also be efficient in yielding small amounts of DNA, typically about 1 ng or less. For analysis of DNA, the yield must be sufficient to allow identification of a sufficient number of genetic features from a fingerprint to allow confident matching with an alleged perpetrator. Typically, matching is done by determining a minimum number of identifiable STR loci from a standard set of loci. At each locus, two alleles are expected, one from each chromosome of an individual. The identification is made difficult by allele drop-outs (e.g., in a heterozygote, only one allele is apparent at a locus) and drop-ins (more than two alleles are apparent). The current method of collecting DNA samples using cotton-tipped swab or cotton pad does not provide for an efficient method of collecting samples from a fingerprint, which may contain fewer than two cells or picograms (pg) quantities of DNA. An efficient and reliable method for recovery of forensic DNA from fingerprints, and release by extraction that allows analysis of the low copy number DNA is therefore highly desirable.

SUMMARY OF THE INVENTION

The invention provides improved materials for collection of trace amounts of DNA for further analysis. More particularly, the invention provides an improved substrate for collection of DNA-containing samples deposited on surfaces and efficient release of the DNA for identification and analysis. In a preferred embodiment, the substrate is cotton yarn. One use for which the invention is particularly suited is collection of DNA evidence from a crime scene, especially DNA from fingerprints such that the amount of DNA recovered is sufficient for amplification so as to allow the alleles identified to be assigned to a locus.

The present invention therefore provides a method for amplification of low copy number of DNA such that the alleles amplified can be definitively assigned to a locus as a homozygote or a heterozygote. The present invention further provides a swab device for maximal recovery of trace amounts of forensic DNA, particularly that from fingerprints.

The invention provides a device for collecting an analyzable amount of DNA from a fingerprint on a surface, comprising a holder member having a first end and second end; and a DNA collecting member adapted to collect and release an analyzable amount of DNA, comprising a cotton yarn having a first end and second end; each end attached to the first end of the holder member, wherein the cotton yarn is not wrapped around the holder member to form a bud. The DNA collecting member can be premoistened, or used to collect a sample that is treated with a sampling solution. Also provided is a method of making the DNA collection device.

The present invention further provides a kit for collecting an analyzable amount of DNA from a fingerprint which includes a container and optionally, swabbing solution. In addition, the invention provides a container designed to prevent contamination of swab following sample collection.

The present invention further provides a method for collecting an analyzable amount of DNA from a surface, comprising contacting a DNA-containing surface comprising a fingerprint with a DNA-collecting device which comprises a holder member having a first end and second end and a collecting member adapted to collect and release an analyzable DNA, comprising cotton yarn having a first end and second end attached to the first end of the holder member, and releasing the collected DNA from the device.

Further, the invention provides a method for analyzing DNA from a fingerprint, comprising collecting fingerprint DNA with a collecting device or the invention, releasing the DNA, and analyzing the released DNA using a high sensitivity PCR DNA testing protocol.

DETAILED DESCRIPTION

To analyze trace DNA samples from surfaces potentially having low copy number (LCN) DNA deposited, it is necessary to maximize both the amount of DNA that is recovered by a sampling device, and the amount of DNA that can be extracted and analyzed from the sampling device.

To improve the collection and analysis of crime scene DNA evidence, the inventors have developed and tested a variety of materials. In particular, in order to perform PCR DNA testing on LCN DNA from fingerprints and other trace evidence, several commercially available materials were tested for their ability to absorb and release DNA in DNA-containing samples, which included skin cells and skin cells deposited on surfaces. All of these materials including tapes, and wipes and swabs composed of microfiber, polyester, foam, natural fabric and DACRON® (DuPont), were tested on fingerprints. (DACRON® is a commonly used swab in forensic laboratories.) In certain tests, the extracted DNA samples were analyzed for the number of correct alleles called and the absence of drop-ins.

It has been found that various cotton yarns, available in many weights and configurations, provide for superior absorption of cells and DNA-containing cell debris, combined with superior release of DNA in extraction procedures. Accordingly, the cotton yarns provide improved substrates for recovery and subsequent release of samples of low copy number (LCN) DNA, particularly from fingerprints and other trace evidence.

The yarn structure provides a large surface area per unit volume. As compared to compact bulb-shaped collection devices (e.g., a Q-TIPS®-like device), yarn fibers are linear and extended with a significantly greater surface to volume ratio. It is considered that the surface area contributed by the yarn fibers is better approximated by extended linear (e.g., tubular) components. The linear components include not only the extended piece of yarn incorporated into the sampling device, but also the multiple plies and fibers of each ply. Without being bound by such a limitation, it is considered that the yarn structure promotes increased absorption and adsorption of biological material, as well as release of nucleic acids during extraction.

A variety of useful cotton yarns are available from various manufactures. In certain embodiments, the yarn is a mixture of cotton with another material, for example, about 50% or greater cotton, or about 85% or more cotton. In another embodiment, the yarn is 100% cotton.

Cotton yarn is spun from discontinuous fibers which range from ¼ inch to more than 12 inches. Multifilament strands may be drawn in the form of sliver, roving, or other suitable forms which are well known. The parallel fibers can be twisted together, or spun, to form the continuous lengths of yarn. Alternatively, a core of parallel fibers which may or may not be twisted, is held together by surface fibers which are helically wound at the exterior surface of the yarn core. Several strands of yarn (plies) may be twisted together to form a cord or rope.

In one embodiment, a yarn can consist of cotton fibers spun into fine threads. The threads are then twisted together to form a yarn. For example, Splendid, which is one of the exemplified yarns, consists of three plies. Each of the plies consists of 9 twisted thread pairs.

Woven yarns can also be used in the invention. Exemplified woven yarns are ROWAN® and CAPRI™, which consist of cotton threads woven into a flat tape.

Also, a variety of yarn weights may be employed. One measure of yarn weight is needle or hook size which relates to the use of a yarn in knitting or crochet. (Knitting requires knitting needles (straight or circular), while crochet uses a crochet hook.) The needle or hook size is determined by the yarn thickness and gauge. "Gauge" is the recommended tension (or number of stitches and rows per inch) that is used when knitting or crocheting a particular yarn and is related to the weight of the yarn. The yarn weight can be any weight that is convenient for forming a swab. In a preferred embodiment, 100 yards of yarn has a weight from about 25 grams up to about 250 grams. More preferably, 100 yards of yarn weighs from about 50 grams to about 100 grams.

Some examples of cotton yarns that can be used according to the invention include, but are not limited to:

BLUE SKY®
Source: Blue Sky Alpacas, Inc.
100% organic cotton
Weight: 100 grams per 150 yards
Gauge: 4 to 5 stitches per inch
Needle size: 7 to 9 US
Color: 80
Lot: 3913
Appearance: A twisted two ply yarn with a traditional ropelike appearance.
Each ply consists of twisted fibers.
CAPRI™
Source: Tahki Yarns, Stacey Charles, Inc.
100% Egyptian cotton
Weight: 50 grams per 52 yards (48 meters)
Color: 001
Lot: 3175
Needle: 13/15 (9-10 mm)
Gauge: 3 stitches per inch
Appearance: flat shoe string with tight weave; smooth
MAYOTTE™
Source: Plassard
100% Cotton
Weight: 50 grams per 90 meters
MAYOTTE™ has a thin thread wrapped around a core of parallel fibers giving it a rope like appearance with fluffy threads (not well defined)
ROWAN®
100% Cotton
Weight: 50 grams per 71 yards (65 meters)
Shade: 540
Lot: 821
Appearance: cotton tape; flat shoestring with loose weave
Splendid
Source: Mondial
100% Egyptian cotton
100 grams, 100 meters
Color: 100
Lot: 49
Appearance: a three-ply yarn with a rope-like appearance; each ply consists of nine pairs of twisted threads.

In a swab of the invention, a length of cotton yarn is affixed to the end of a holder. In one embodiment, the cotton yarn is formed into a loop and affixed at its free ends to the holder. By forming a loop, fraying of the yarn is avoided, and a more resilient self-supporting structure is provided for contacting the sample collection surface. In another embodiment of the invention, a length of yarn is twisted or curled to form a small ball and affixed at its free ends to the holder. In another embodiment of the invention, the yarn is folded to resemble a fan, having two or more loops, and affixed by its ends and the base of the loops to the holder. In a particular embodiment, the yarn extends from the end of the holder, attached to the holder only at discrete points (e.g., at the yarn ends for a single loop or ball). Such an attachment allows easy separation of the major portion of the collection surface from the holder for sample extraction (for example, by detachment of the yarn at the holder end). Any tendency of the yarn to fray upon cleavage may be beneficial for extraction.

Although any length of yarn can be used, the length should be chosen to be convenient for sample collection and extraction. For example, when used with an automated extraction procedure or a robotic pipettor, it is often desirable to minimize the amount of cotton in an extraction procedure so as to avoid interference with the pipettor. As the volume of cells and/or DNA to be collected from a fingerprint is small, there is no need for large yarn amounts. For example, as can be seen from experimental data set forth below, the yield of DNA from certain samples using a 1 cm length of yarn was not appreciably different from the yield of DNA using a 3 cm length of yarn. In a preferred embodiment, the yarn length is from about 0.5 cm to about 3 cm. In a more preferred embodiment, the yarn length is from about 0.75 cm to about 2 cm. In a particularly preferred embodiment, the yarn length is about 1 cm.

In an embodiment of the invention, a length of MAYOTTE™ (PLASSARD™) yarn (U.S. needle size 7) is attached to a holder in the form of a loop having a diameter of about 0.5 cm. After sample collection, the loop is cut from the holder, yielding a yarn fragment of about 1.3 cm, from which nucleic acids are extracted. The combination of yarn weight, form, and fragment length allows for convenient centrifugation of the extraction solution in a 1.5 ml microfuge tube such that the yarn fragment is displaced to the bottom of the tube so as not to interfere with a robotic pipetting apparatus.

The swab holder can be any material useful as a holder for the collection of samples on or in swabs. The present invention contemplates the use of materials including, but not limited to wood, plastics, resins, and various synthetic material. The holder may be rigid or flexible. In a preferred embodiment, the holder is of a material that does not absorb moisture. In a preferred embodiment, the holder is made of polypropylene or other plastic that minimally absorbs or binds to DNA. The holder may be designed such that the swab head is easily separated for sample processing. In addition, the holder may be designed to allow easy attachment of the swab head by simply tying, gluing or heat-shrinking to the holder.

For sampling of fingerprints, it is usually preferred to use the swab with a sample collection medium (or "swabbing solution"). The medium can be used to wet the fingerprint prior to swabbing. Alternatively, the swab can be moistened at the time of sample collection by wetting the swab with a solution prior to contacting the fingerprint. The solution may be stored in a container, such as, but not limited to, a dropper bottle. In such a manner, the swabbing solution maintains sterility and avoids contact with outside contaminants. Alternatively, the swab can be provided pre-moistened in a sealed package that is opened at the time of sampling.

A variety of swabbing solutions can be used, which include, but are not limited to, phosphate buffered saline (PBS), different concentrations of isopropanol, ethanol, and SDS. Currently, 0.01% SDS is the preferred swabbing solution. Swabbing solution may also include lipids, enzymes and other substances commonly found in skin.

A forensic swab used for retrieval and analysis of human DNA is manufactured as sterile swab using methods known in the art, such as but not limited to UV irradiation, and heat or chemical sterilization. The swab should also be free of human DNA when manufactured and should be handled aseptically to prevent contamination from other human sources during the entire sampling and processing processes.

To prevent contamination, the invention provides a container into which a sample-containing crime scene swab may be inserted for storage and transport. The container is designed to readily accept the swab and prevent contact with contaminants (e.g., cross-contamination with other samples or contamination from personnel present at the crime scene investigation).

In an embodiment of the invention, the container is a box that contains a retainer into which the holder of the swab is inserted. The retainer can be, for example, a styrofoam block. The styrofoam holds the swab in position, such that the swab head does not contact the walls of the container. In one preferred embodiment, the container has a square cross section. In another embodiment, the container has a round cross section. A cap is provided that engages the open end of the container to prevent contamination of the swab head from external sources. The container can be made of any material and may be disposable. Optionally, the container may be designed to promote or prevent drying of the sample-containing swab. In one preferred embodiment that allows for drying, the container is cardboard. In another embodiment, the container is perforated. In yet another embodiment, the container includes a desiccant.

In another embodiment, the swab and portions of the container are integrated. For example, the end of the swab holder opposite from the swab head is attached to a container cap of square or circular cross section. A square or cylindrical container tube, closed at one end, is engagingly fitted to the combined swab and cap. At the crime scene, the container parts are separated, the sample collected, and the swab and cap re-engaged with the tube. As above, the container may be designed to promote or prevent drying of the sample-containing swab.

The swab of the invention or a container for protection or storage of the swab (or both the swab and container) preferably includes a feature to facilitate identification of the sample. In one embodiment, a means of identification feature is attached to the container. In a second embodiment, the identification feature is attached to, or is an integral part of the swab. Non-limiting identification features include, but are not limited to, labels which may be handwritten, bar codes, radio frequency identification (RFID) tags, and the like. Information to be recorded for each sample or group of samples would include, for example, the name of a crime scene analyst, precinct, complaint number, victim identification, the swab type, and crime scene information, such as other persons present, the presence of fingerprint powder, and the like.

The swabs of the invention can be used in high sensitivity PCR DNA testing protocols. PCR DNA testing according to the high sensitivity PCR DNA testing protocol produces full STR profiles from amplification of as little as 25 pg of DNA, or four cells, and partial profiles from about 12.5 pg of DNA, in a high throughput manner. The method uses a simple extraction with detergent followed by concentration. Quantitation by real time PCR of ALU sequences allows negative samples can be eliminated. Positive samples are then amplified with a commercially available human STR megaplex kit such as AMPF1STR® IDENTIFILER® PCR Amplification Kit (ABI) or POWERPLEX® 16 System (Promega). Optimized data analysis produces CODIS, or database, eligible DNA profiles while compensating for artifacts of low level DNA amplification.

The DNA-containing sample is extracted from the swab of the invention by incubating the sample-containing swab in a sample buffer for a time sufficient to release nucleic acids. In an embodiment of the invention, the sample buffer comprises SDS and Proteinase-K. In one example, a sample-containing swab (which may be separated from the holder) is incubated in 200 μL of 0.01% SDS and 0.18 mg/ml Proteinase K at 56° C. for two hours with shaking at 1400 rpm, followed by a 10 mins. incubation at 99° C. In another embodiment of the invention, the sample-containing swab is incubated in 200 μL of 0.05% SDS and 0.72 mg/ml Proteinase K at 56° C. for 30 mins. with shaking at 1400 rpm, followed by a 10 mins. incubation at 95° C. Selection of the preferred sample buffer can be determined by a skilled artisan based upon consideration of several factors, including the type of detergent and protease used, the size of the swab or collecting member, the sample size etc.

The digest is added to either a MICROCON®-100 or a MICROCON®-50 microconcentrator pretreated with 200 μL of water containing 1 ng of poly-A RNA to prevent DNA loss, and centrifuged for 15 mins. at 2400 rpm. The DNA is then eluted in 20-25 μL of water for 3 mins. at 3600 rpm. The volume of the elutant is dependent on the volume of the DNA template required for amplification with a half reaction of the POWERPLEX® DNA typing kit or IDENTIFILER® kit. Alternatively, the eluted DNA can be precipitated with isopropanol, washed with ethanol and stored before amplification.

The swab of the present invention provides for recovery and release of low copy number (LCN) DNA in an analyzable amount to enable identification of multiple loci for comparison to a crime database. In an embodiment of the invention, an analyzable sample allows identification of four or more loci. In New York State, to be compared to a DNA profile database, samples from an alleged perpetrator must yield six or more loci. Accordingly, in another embodiment of the invention, an analyzable sample provides for identification of six or more loci. High sensitivity PCR amplification methods (e.g., IDENTIFILER® and POWERPLEX®) can provide STR profiles from as little as 12.5 pg of DNA or less. As exemplified herein, the yield of DNA from fingerprints ranged from about 10 pg to about 60 pg.

Methods of STR analysis are known in the art, and kits and reagents are commercially available. For example, the POWERPLEX® 16 system (Promega) is a multiplex STR system for use in DNA typing, including forensic DNA analysis. This system allows the co-amplification and three-color detection of fifteen STR loci (Penta E, D18S51, D21S11, TH01, D3S1358, FGA, TPDX, D8S1179, vWA, Penta D, CSF1PO, D16S539, D7S820, D13S317 and D5S818) and Amelogenin. All sixteen loci are amplified simultaneously in a single tube and analyzed in a single injection (genetic analyzer) or sequencing gel lane.

The swabs and containers may be individually packaged, or assembled into kits. Such kits may additionally contain any accessories necessary for sample collection. Such accessories include swabbing solution, labels, instructions, and other documents. The size of the kit (i.e., the number of samples per kit) will be dictated by crime scene data collection protocols. For example, one kit that is currently being evaluated contains six swabs because the DNA typing laboratory agreed to type six samples per burglary.

Of course, it is to be understood and expected that variations in the principles of the invention herein disclosed can be made by one skilled in the art and it is intended that such modifications are to be included within the scope of the present invention.

All references mentioned herein are incorporated in their entirety.

EXAMPLES

The following examples further illustrate the invention, but should not be construed to limit the scope of the invention in any way.

Example 1

Comparison of Swab Materials for Generation of DNA Profiles from Fingerprints

Fingerprints of donors (ten fingers) were deposited on chrome doorknob. The prints were swabbed with approximately 1 cm length of a DACRON® swab or pieces of ROWAN® yarn, cotton wipe, microfiber (streetfair), microFiber (sa-73481e), heavy polyester (sa6254), and light polyester (sa6209) moistened with 0.01% SDS.

Samples materials were incubated in 200 μl of 0.01% SDS and 0.18 mg/ml Proteinase K for two hours at 56° C. with shaking at 1400 rpm, followed by 10 mins. at 99° C. Two hundred μl of water and the 200 μl of sample were added to a MICROCON®-100 and centrifuged for 15 mins. at 2400 rpm. DNA was eluted with 50 μl of water for 3 mins. at 3500 rpm.

A 10 μl sample was amplified with POWERPLEX® 16 (Promega) according to the manufacturer's instructions, except that 35 cycles were employed. Two μl of the amplification reaction products were injected on an ABI Prism 3100 for 20 sec at 3 kV.

Values are expressed as the percentage of correct allelic determinations (mean+/−standard deviation) for 5 experiments with 95 fingerprint samples (ROWAN® cotton yarn: n=38; light polyester: n=13; heavy polyester: n=12; cotton wipe: n=10; street fair and SA73481e microfiber: n=8; DACRON®: n=6).

Figure 1:
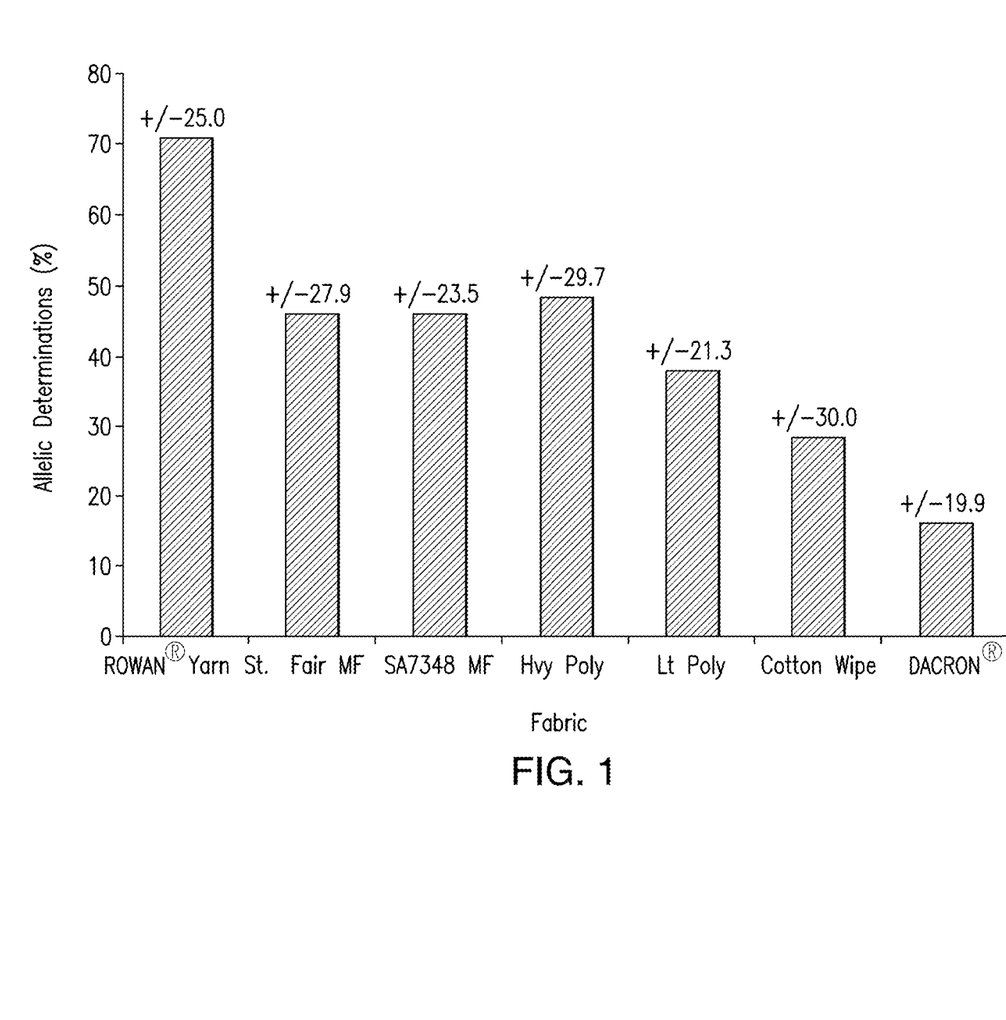
FIG. 1 shows DNA profile results for fingerprints obtained from a smooth surface (chrome doorknob) using various swab materials (ROWAN® 100% cotton yarn, St. Fair microfiber, SA7348 microfiber, heavy polyester, light polyester, cotton wipe, DACRON®)

The cotton yarn produced the most allelic calls (70.7+/−25.83%). (FIG. 1) The next group of four fabrics provided similar results that were inferior to the cotton yarn: streetfair microfiber (46+/−28%); sa73481e microfiber (46+/−23.5%); heavy polyester (48.4+/−29%); light polyester (38+/−21%). The cotton wipe produced only 28.3+/−30% correct calls, and the DACRON® swab generated only 16.1+/−19.9% correct calls. Further, the results for the cotton yarn were superior to the best microfiber swab candidate (swab ss-1) which generated 56+/38% correct allelic determinations on the surface of the chrome doorknob (not shown).

Example 2

Comparison of Swab Materials—DNA Sample Absorption

Absorption of DNA in a DNA solution was determined. A 4 ng DNA sample in 10 μl of water was placed in a microfuge tube. Cotton materials approximately 1 cm were placed in the tubes for 10 mins. at room temperature and then removed. Two hundred μl of water was added to the tubes to resuspend any remaining DNA. After incubation for 20 mins. At room temperature, the samples were concentrated to 25 μl with a MICROCON®-100 microconcentrator. The amount of DNA in the samples was determined with ALU based real time PCR. Results are expressed as the amount of DNA measured divided by the starting amount of DNA.

Figure 2:
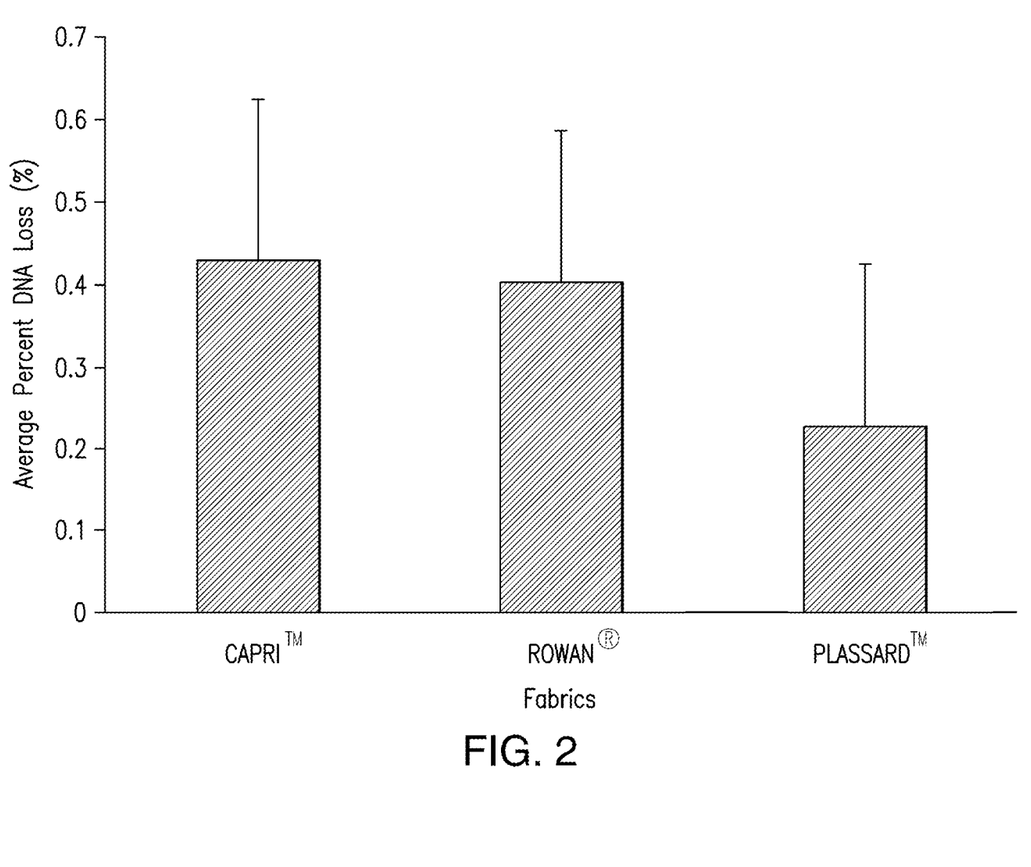
FIG. 2 shows the results of a DNA loss experiment that measured DNA remaining in a tube following absorption of a DNA solution using various cotton yarns.

Very little of the DNA in the microfuge tubes was not absorbed by the cotton swab materials. (FIG. 2) The amounts of DNA remaining were 0.22+/−0.19% (MAYOTTE™/PLASSARD™), 0.42+/−0.19% (CAPRI™) and 0.4+/−0.18% (ROWAN®).

Comparison of Swab Materials—DNA Release from Swab

Figure 3:
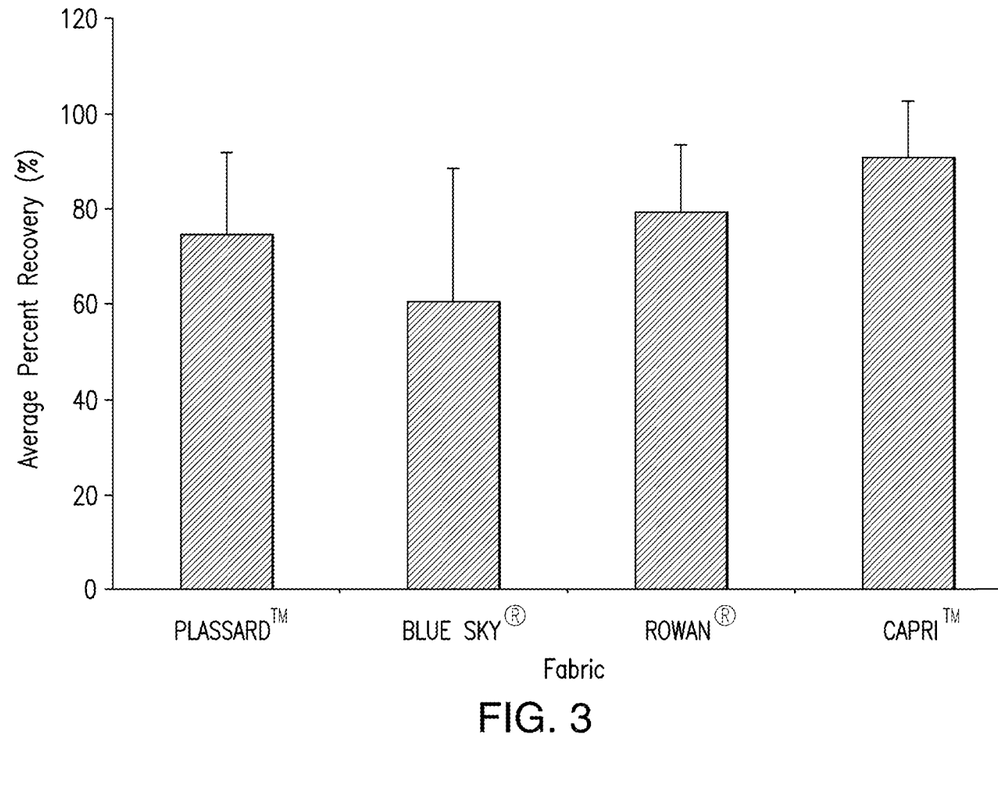
FIG. 3 shows the results of a DNA loss experiment that measured irreversible binding of DNA to various cotton yarns.

DNA lost to the various swab types was determined. 1600 pg of DNA in 5 µl were applied directly to each of the cotton yarns (CAPRI™, MAYOTTE™/PLASSARD™, BLUE SKY®, ROWAN®), and incubated for 10 mins. at room temperature. The swab materials were added to microfuge tubes with 200 µl of water, and shaken for 20 mins. at room temperature. The amount of DNA in the samples was determined with ALU based real time PCR. The amount of DNA in the samples was compared to the DNA applied to each material sample (5 µl; 1600 pg). (FIG. 3) Results expressed as mean percent recovery+/−SE were as follows: the DNA recovery from the various cotton yarns was 90+/−12% (CAPRI™; n=9), 74+/−17% (MAYOTTE™/PLASSARD™; n=6), 87+/−14% (ROWAN®; n=9) and 60+/−28% (BLUE SKY®; n=3)

Comparison of Swab Materials—Recovery and Release of Cells

5 µl of cells (about 150 cells/µl) were placed on a bench top, dried and swabbed with approximately one inch of a candidate swab material with 0.01% SDS, and extracted as follows: swab materials were incubated in 200 µl of 0.01% SDS and 0.18 mg/ml Proteinase K for two hours at 56° C. with shaking, followed by 10 mins. at 99° C. For a positive control, the extraction procedure was performed on 5 µl of cells placed directly in a microfuge tube. For substrate controls, 5 µl of cells were applied directly to the various swab materials.

For each sample, 200 µl of water with 1 ng poly-A mRNA was first added to a MICROCON®-100 microconcentrator followed by the 200 µl sample. The microconcentrators were centrifuged for 15 mins. at 2400 rpm, and the concentrated solution was eluted with 20-25 µl of water for 3 mins. at 3500 rpm.

Final elution volumes were recorded. The amount of DNA in 2.5 µl of the elutant was determined with ALU based real time PCR. The Alu fragment is amplified and compared to a standard curve according to the method described in Nicklas and Buel (J. Forensic Sci. 48:282 (2003)). DNA recovery was expressed as mean+/−SD of the amount of DNA recovered from the swab divided by the substrate control. DNA release was expressed as mean+/−SD of the substrate control divided by the positive control.

Figure 4A:
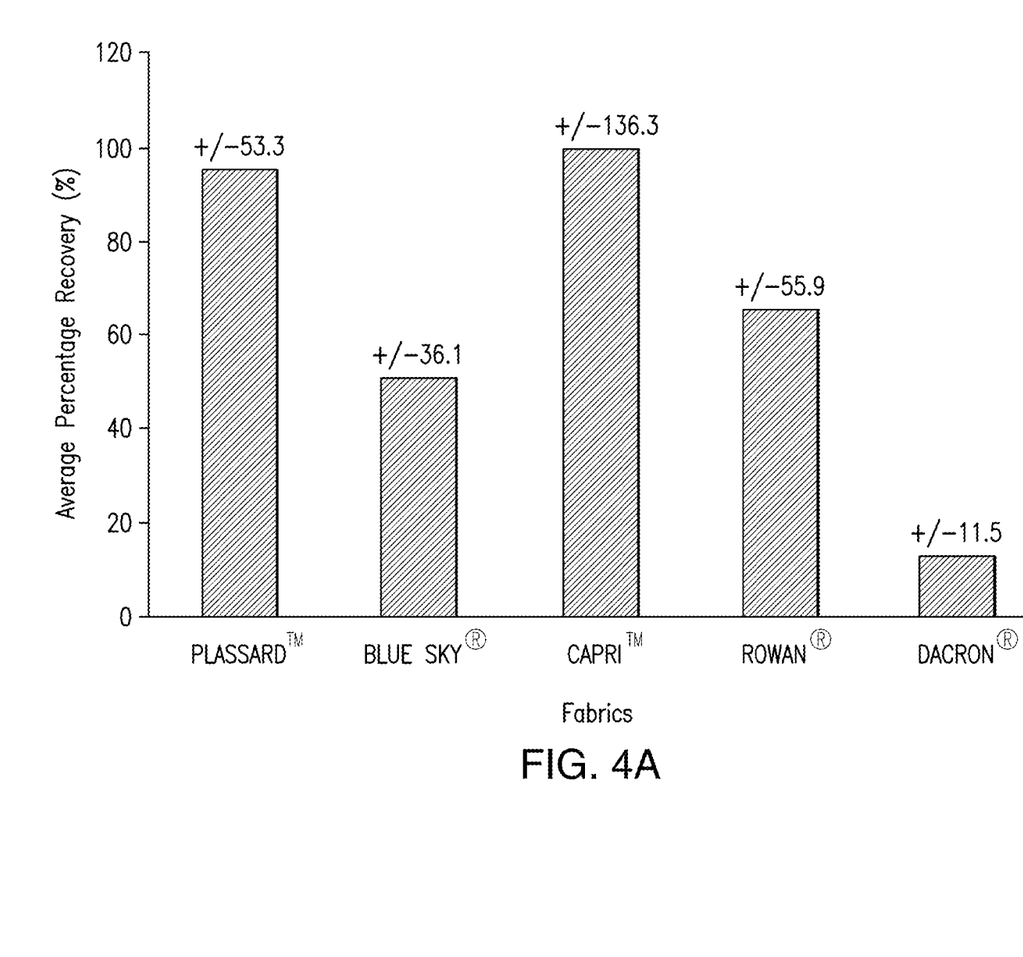
FIG. 4a depicts recovery of DNA from a cell sample deposited on a solid surface, swabbed, and extracted, as compared to DNA extractable from an equivalent cell sample applied directly to a swab, for four cotton yarns and DACRON®.

DNA recovery (the proportion of DNA swabbed from benchtop relative to the amount deposited directly on the surface of a swab [substrate control]; FIG. 4a) from the various cotton yarns was 95+/−55.3% (MAYOTTE™/PLASSARD™), 100+/−135% (CAPRI™), 65.5+/−55.98% (ROWAN®) and 50.6+/−36.1% (BLUE SKY®). Recovery from the DACRON® swab material was 13.3+/−11.5%.

Figure 4B:
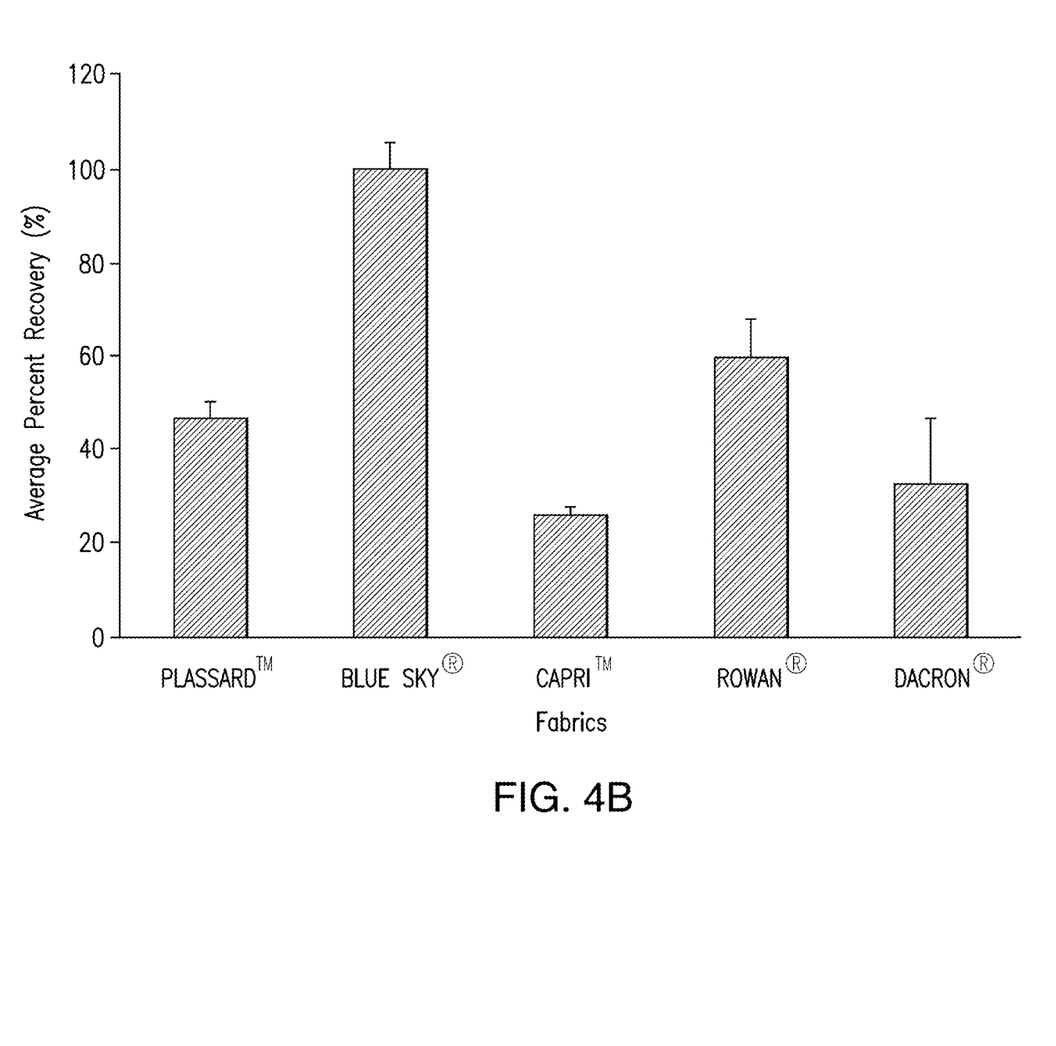
FIG. 4b depicts release of DNA extracted from cells absorbed onto one of four cotton yarns or DACRON, as compared to DNA extracted directly from an equivalent cell sample.

DNA release (the proportion of DNA added directly to a swab and released relative to the amount of DNA added to the swab [substrate control]; FIG. 4b) from the various cotton yarns was 99.8+/−5.4% (BLUE SKY®), 59.1+/−8.5% (ROWAN®), 46.2+/−3.7% (MAYOTTE™/PLASSARD™) and 25.2+/−1.8% (CAPRI™). Recovery from the DACRON® swab material was 31.7+/−14%.

Yield is the amount of DNA available for analysis by PCR and is a product of recovery and release from the swab. All four cotton yarns yielded a significantly higher proportion of the DNA from the cell samples placed on the bench-top than the DACRON® material. The overall yield for the cotton yarns ranged from about 25 to about 50%, whereas the yield of the DACRON® material was about 4%.

Determination of Optimal Swab Size

Ten µl of cells were pipetted onto a cookie sheet and allowed to dry. The samples were swabbed with either 1 cm, 2 cm, or 3 cm of cotton yarn (MAYOTTE™/PLASSARD™ or CAPRI™) with 0.01% SDS. Samples were extracted by incubation in 200 µl of 0.01% SDS and 0.18 mg/ml Proteinase K for two hours at 56° C. with shaking, followed by 10 mins. at 95° C. For each sample, 200 µl of water with 1 ng polyA mRNA was first added to a MICROCON®-100 microconcentrator followed by the 200 µl sample. The microconcentrators were centrifuged for 15 mins. at 2400 rpm, and the concentrated solution was eluted with 25 µl of water for 3 mins. at 3500 rpm.

Final elution volumes were recorded. The amount of DNA in 2.5 µl of the elutant was determined with ALU based real time PCR. DNA recovery was expressed as pg/µl for means+/−SE, where n=3 for two experiments.

The MAYOTTE™/PLASSARD™ yarn yields were 1083.5+/−486 pg/µl (1 cm), 776+/−510 pg/µl (2 cm), and 862+/−437 pg/µl (3 cm). The CAPRI™ yarn yields were 867+/−551 pg/µ (1 cm), 586+/−193 pg/µl (2 cm), and 638+/−183 pg/µl (3 cm).

Recovery and Release of DNA from Fingerprints

Two fingerprint donors placed their fingerprints on a cookie sheet. The prints were swabbed with approximately 1 cm of cotton yarn (MAYOTTE™/PLASSARD™ or CAPRI™) with forceps and 0.01% SDS. Swabs were gently rubbed over fingerprints until the prints were no longer evident.

Samples were extracted by incubation in 200 µl of 0.01% SDS and 0.18 mg/ml Proteinase K for two hours at 56° C. with shaking, followed by 10 mins. at 99° C. For each sample, 200 µl of water with 1 ng polyA mRNA was first added to a MICROCON®-100 microconcentrator followed by the 200 µl sample. The microconcentrators were centrifuged for 15 mins. at 2400 rpm, and the concentrated solution was eluted with 25 µl of water for 3 mins. at 3500 rpm.

Final elution volumes were recorded. The amount of DNA in 2.5 µl of the elutant was determined with ALU based real time PCR (Table 1). DNA yield from each fingerprint is expressed as pg/µl for means+/−SE, where n=20 for two experiments for CAPRI™ cotton yarn and n=20 for three experiments for MAYOTTE™/PLASSARD™ cotton yarn.

TABLE 1

DNA recovery from fingerprints
(pg/µl; 25 µl per fingerprint)

| | MAYOTTE ™/ PASSARD ™ | CAPRI ™ |
| --- | --- | --- |
| left thumb (LT) | 2.5 +/− 2.0 | 3.2 +/− 4.5 |
| left index (LI) | 1.3 +/− 0.6 | 2.2 +/− 3.1 |
| left middle (LM) | 1.4 +/− 0.9 | 0.9 +/− 1.0 |
| left ring (LR) | 0.7 +/− 0.4 | 0.4 +/− 0.3 |
| left pinkie (LP) | 0.9 +/− 0.6 | 0.5 +/− 0.3 |
| right thumb (RT) | 2.5 +/− 1.7 | 1.1 +/− 1.0 |
| right index (RI) | 22.5 +/− 35.7 | 0.7 +/− 0.3 |
| right middle (RM) | 1.0 +/− 0.8 | 0.9 +/− 0.6 |

TABLE 1-continued

DNA recovery from fingerprints
(pg/μl; 25 μl per fingerprint)

|  | MAYOTTE™/ PASSARD™ | CAPRI™ |
| --- | --- | --- |
| right ring (RR) | 0.5 +/− 0.3 | 0.4 +/− 0.2 |
| right pinkie (RP) | 0.5 +/− 0.2 | 0.6 +/− 0.3 |

Construction of a DNA Swab

Figure 5A:
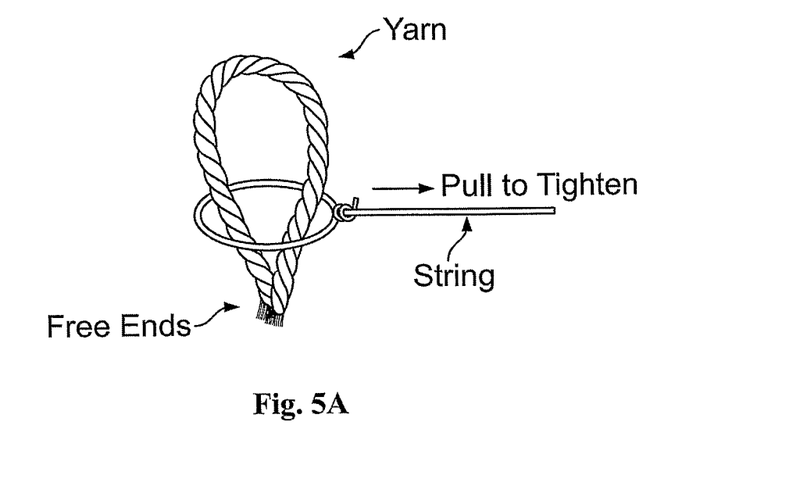
FIG. 5A illustrates formation of a fabric loop in a forensic swab of the invention.
Figure 5B:
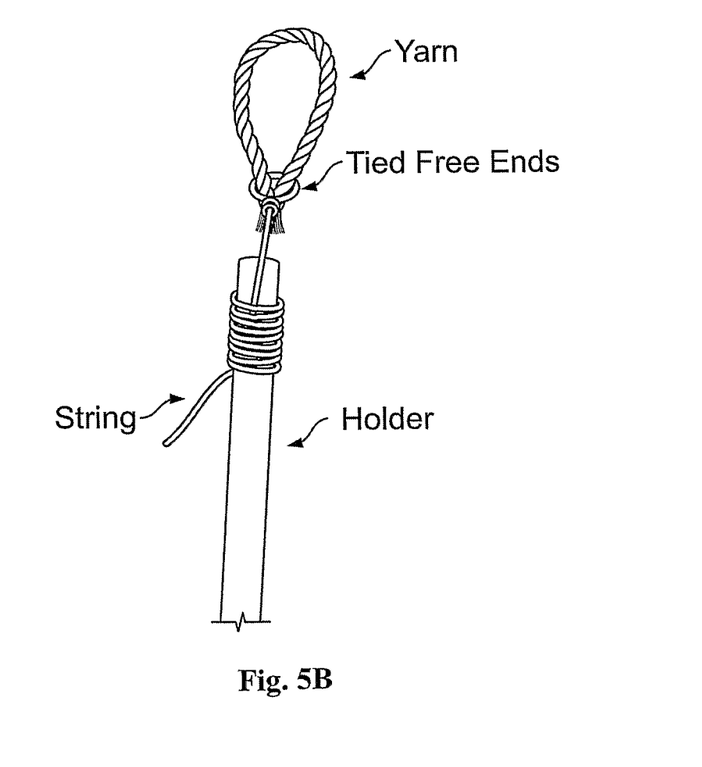
FIG. 5B illustrates attachment of the swab head onto a holder via a heat shrink tubing.
Figure 5C:
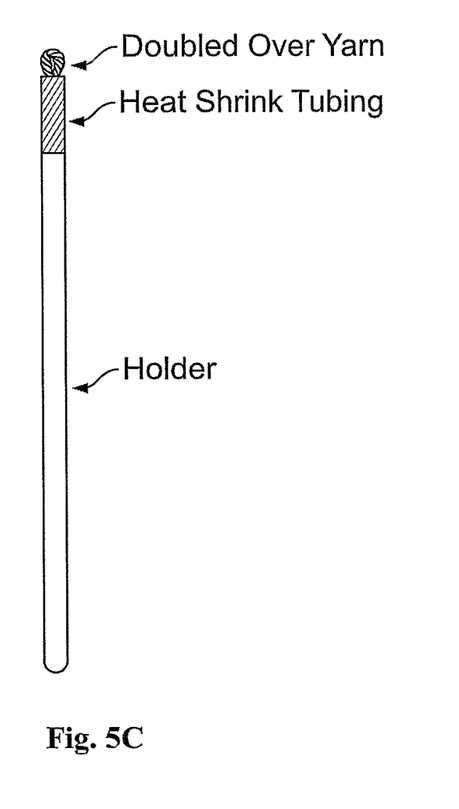
FIG. 5C shows a complete swab comprising sampling fabric, heat shrink tubing, and rigid plastic holder.

A prototype swab was constructed by doubling MAYOTTE™/PLASSARD™ yarn. The free ends were tied together with a small diameter thread. The string was threaded through heat shrink tubing and both were drawn over the end of a plastic holder, trapping the string and the free ends of the yarn between the tubing and the holder. When the heat shrink tubing was exposed to heat, a tight seal is formed around the fabric and holder. (FIG. 5) The swab may be adapted to collect and release an analyzable amount of about 100 pg of DNA or less, 50 pg of DNA or less, 25 pg of DNA or less, or 12.5 pg of DNA or less.

Storage Containers

Figure 6:
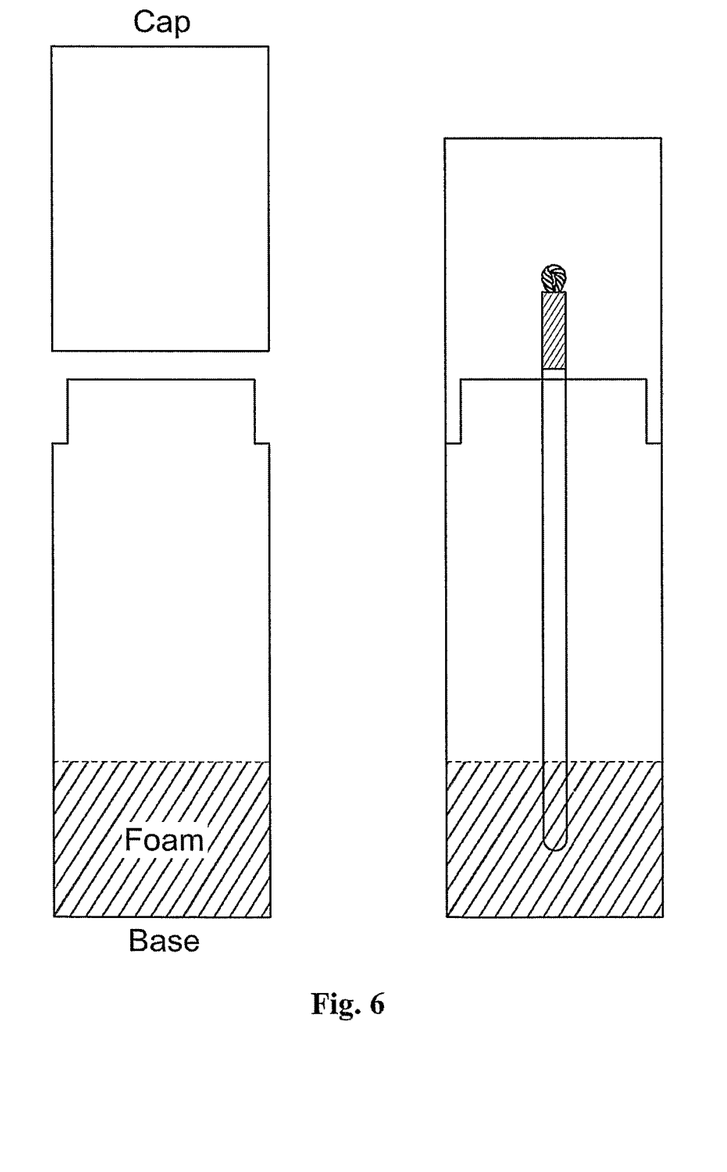
FIGS. 6 and 7 illustrate sample containers for storing a swab containing a forensic DNA sample.

A rectangular cardboard container is used to store a DNA swab during transport from the crime scene to the laboratory. The base of the container contains foam that is easily pierced by the holder of the swab. When inserted into the foam, the swab is prevented from touching the sides of the container. A cardboard cap fits over the opening of the container to prevent contamination of the collected sample. (FIG. 6)

Figure 7:
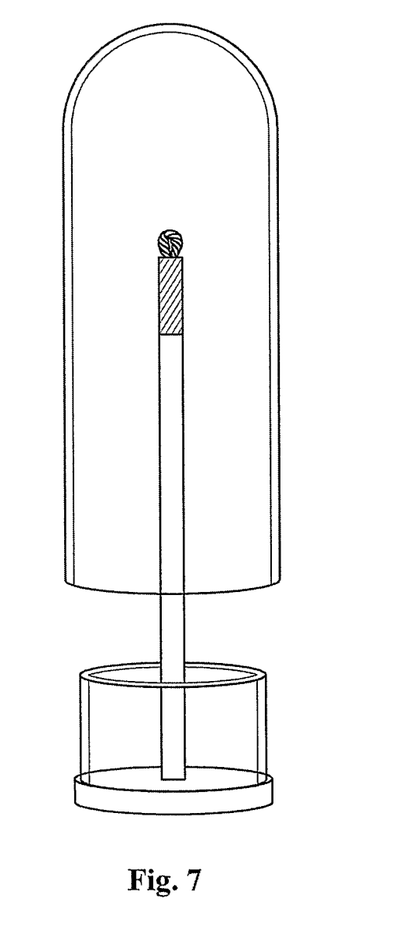

Another example of a convenient storage container is depicted in FIG. 7. The swab holder is integrated with the cap of the storage container. The container is disengaged from the cap for sample collection, and engaged for storage.

We claim:

1. A device for collecting an analyzable amount of sample DNA from a fingerprint on a surface, comprising:
   (a) a holder member having a first end and second end; and
   (b) a DNA-collecting member adapted to collect and release an analyzable amount of DNA, the DNA-collecting member comprising a single, twisted cotton yarn loop having a first end and second end;
   at least one string structure (i) tying together the first end and the second end of the cotton yarn loop, and (ii) coupling the cotton yarn loop to the first end of the holder member; and
   heat shrink tubing structure affixing (i) at least the first end and the second end of the cotton yarn loop to the first end of the holder member, and (ii) the at least one string structure to the first end of the holder member.

2. The device of claim 1, wherein the DNA-collecting member is pre-moistened.

3. The device of claim 1, wherein the cotton yarn is rope-like.

4. The device of claim 1, wherein the cotton yarn is woven.

5. The device of claim 1, wherein the cotton yarn has a weight of about 0.25 g/yd to about 2.5 g/yd.

6. The device of claim 1, wherein the collecting member comprises means for collecting and releasing an analyzable amount of about 100 pg of DNA or less.

7. The device of claim 1, wherein the collecting member comprises means for collecting and releasing an analyzable amount of about 50 pg of DNA or less.

8. The device of claim 1, wherein the collecting member comprises means for collecting and releasing an analyzable amount of about 25 pg of DNA or less.

9. The device of claim 1, wherein the collecting member comprises means for collecting and releasing an analyzable amount of about 12.5 pg of DNA or less.

10. The device of claim 1, wherein the collecting member comprises means for providing a yield of at least 25% of the available DNA in the sample.

11. The device of claim 10, wherein the collecting member comprises means for providing a yield of at least 50% of the available DNA in the sample.

12. The device of claim 1, wherein the DNA-collecting member is disposed in a loop at the first end of the holder.

13. The device of claim 1, wherein the DNA-collecting member has a length of 0.5 cm to 3 cm.

14. The device of claim 1, wherein the DNA-collecting member has a length of 0.75 cm to 2 cm.

15. The device of claim 1, wherein the DNA-collecting member has a length of 1 cm.

16. A kit for collecting an analyzable amount of sample DNA from a surface, comprising:
   (a) a DNA-collecting device; wherein the device comprises
      (i) a holder member having a first end and second end,
      (ii) a DNA-collecting member adapted to collect and release an analyzable amount of DNA from the fingerprint, the DNA-collecting member comprising a single, twisted cotton yarn loop having a first end and a second end, (iii) at least one string structure (iiia) tying together the first end and the second end of the cotton yarn loop, and (iiib) coupling the cotton yarn loop to the first end of the holder member, and (iv) heat shrink tubing structure affixing (iva) at least the first end and the second end of the cotton yarn loop to the first end of the holder member, and (ivb) the at least one string structure to the first end of the holder member; and
   (b) a receptacle for retaining the DNA-collecting device of (a).

17. The kit of claim 16, further comprising a swabbing solution.

18. The kit of claim 17, wherein the swabbing solution comprises SDS.

19. The device of claim 16, wherein the DNA-collecting member is disposed in a loop at the first end of the holder.

20. The device of claim 16, wherein the DNA-collecting member has a length of 0.5 cm to 3 cm.

21. The device of claim 16, wherein the DNA-collecting member has a length of 0.75 cm to 2 cm.

22. The device of claim 16, wherein the DNA-collecting member has a length of 1 cm.

23. A device for collecting an analyzable amount of sample DNA from a fingerprint on a surface, comprising:
   (a) a holder member having a first end and second end; and
   (b) a DNA-collecting member adapted to collect and release an analyzable amount of DNA from the sample, comprising:
      a cotton yarn disposed in a single loop and having a first end and second end;
      at least one string coupling both ends of the cotton yarn single loop to the first end of the holder member;
      heat-shrink material affixing (i) both ends of the cotton yarn single loop and (ii) the at least one string to the first end of the holder member.

* * * * *